(12) United States Patent
Rhode et al.

(10) Patent No.: US 7,504,264 B2
(45) Date of Patent: Mar. 17, 2009

(54) METHOD FOR CHARACTERIZING A HIGHLY PARALLELIZED LIQUID HANDLING TECHNIQUE USING MICROPLATES AND TEST KIT FOR CARRYING OUT THE METHOD

(75) Inventors: Heidrun Rhode, Hainichen (DE); Anton Horn, Jena (DE); Barbara Horn, legal representative, Jena (DE); Margarete Schulze, Jena (DE); Gerhard Cumme, Jena (DE)

(73) Assignee: CyBio AG, Jena (DE)

( * ) Notice: Subject to any disclaimer, the term of this patent is extended or adjusted under 35 U.S.C. 154(b) by 831 days.

(21) Appl. No.: 10/507,553

(22) PCT Filed: Mar. 13, 2003

(86) PCT No.: PCT/DE03/00834

§ 371 (c)(1),
(2), (4) Date: May 23, 2005

(87) PCT Pub. No.: WO03/079030

PCT Pub. Date: Sep. 25, 2003

(65) Prior Publication Data

US 2006/0063272 A1    Mar. 23, 2006

(30) Foreign Application Priority Data

Mar. 14, 2002  (DE) ............................... 102 12 557

(51) Int. Cl.
*G01N 21/03* (2006.01)
*G01N 21/75* (2006.01)
*G01N 21/76* (2006.01)

(52) U.S. Cl. .................. 436/165; 436/164; 436/166; 436/172

(58) Field of Classification Search ................. 436/180, 436/164–166, 172
See application file for complete search history.

(56) References Cited

U.S. PATENT DOCUMENTS 4,354,376 A   10/1982   Greenfield et al.

(Continued)

FOREIGN PATENT DOCUMENTS

DE    199 28 056    12/2000
WO    WO 97/15394    5/1997

*Primary Examiner*—Brian R. Gordon
(74) *Attorney, Agent, or Firm*—Reed Smith LLP

(57) ABSTRACT

A method for characterizing highly parallelized liquid handling technology using microplates and test kit for carrying out the method. Possibilities for characterizing a multi-channel or many-channel handling technology are known in principle. However, especially with regard to more highly parallelized devices and very small volumes, particularly under conditions corresponding to the actual application conditions, these possibilities were relatively expensive and presented problems especially with respect to the accuracy of evaluation and with respect to correctness and precision. The present method enables a more economical and very exact characterization for applications of this kind. According to the invention, a) a mean sample volume or mean reagent volume is determined by gravimetry from the totality of sample liquid or reagent liquid of all individual channels of the liquid handling technology; b) a normalized mean optical intensity is formed from optical measurement signals of all sample volumes or reagent volumes, each of which is mixed with a diluent; c) the volume accuracy of every individual channel of the liquid handling technology with respect to the mean sample volume or mean reagent volume is determined from the intensity deviation of the normalized optical measurement signal of the individual channel in relation to the normalized mean optical intensity. Further, a test kit is provided for advantageous implementation of the method. The invention is used wherever highly parallelized liquid handling technology is to be characterized with respect to accuracy and precision, particularly when the handled volumes lie within the μl range or sub-μl range and characterization is to be carried out under conditions approximating the real operating conditions.

29 Claims, 5 Drawing Sheets

Temperature dependence of p-nitrophenol absorbance
in diethanolamine buffer (Application Example 4)

U.S. PATENT DOCUMENTS

| | | |
|---|---|---|
| 5,492,673 A | 2/1996 | Curtis et al. |
| 5,965,453 A | 10/1999 | Skiffington et al. |
| 6,188,476 B1 | 2/2001 | Hafeman et al. |
| 6,741,365 B2 | 5/2004 | Curtis |
| 6,890,485 B1 * | 5/2005 | Stylli et al. .................. 506/39 |
| 7,187,455 B2 | 3/2007 | Curtis |
| 2002/0012611 A1 * | 1/2002 | Stylli et al. .................. 422/65 |
| 2002/0149772 A1 | 10/2002 | Halg |
| 2005/0130318 A1 * | 6/2005 | Vann et al. .................. 436/180 |
| 2005/0226771 A1 * | 10/2005 | Lehto et al. .................. 422/63 |
| 2005/0233472 A1 * | 10/2005 | Kao et al. .................. 436/180 |
| 2007/0015289 A1 * | 1/2007 | Kao et al. .................. 436/180 |

* cited by examiner

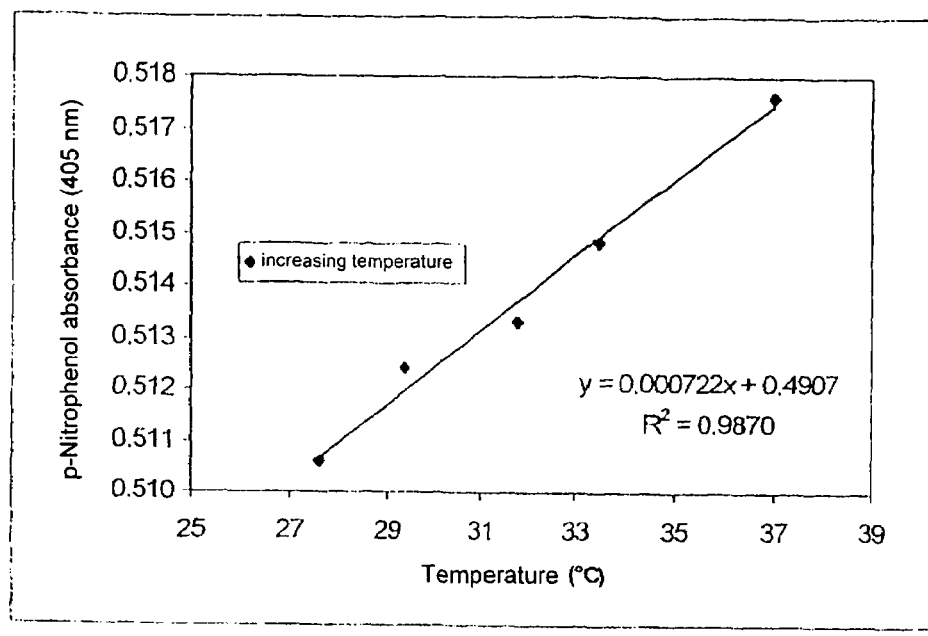
Fig. 1: Temperature dependence of p-nitrophenol absorbance in diethanolamine buffer (Application Example 4)
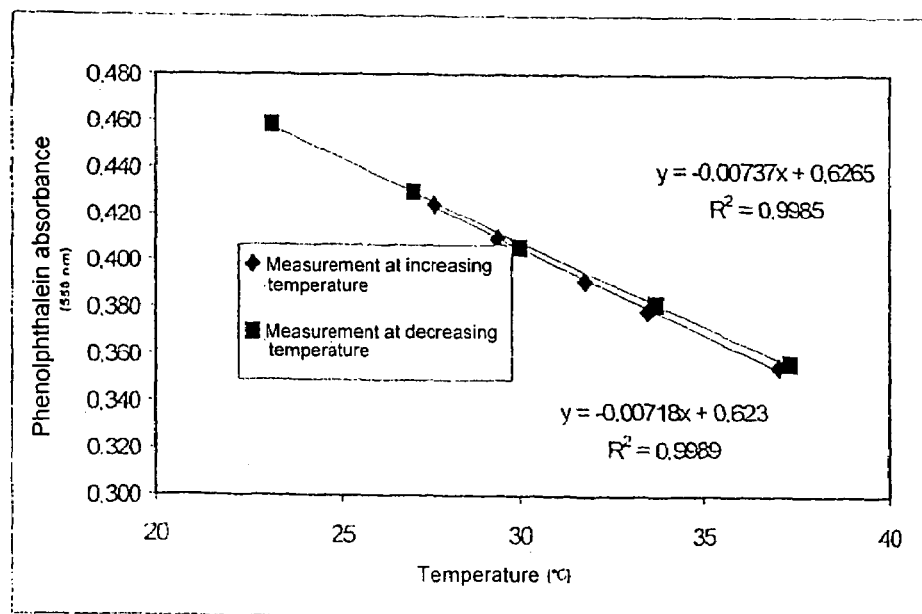
Fig. 2: Temperature dependence of phenolphthalein absorbance in diethanolamine buffer (Application Example 4)

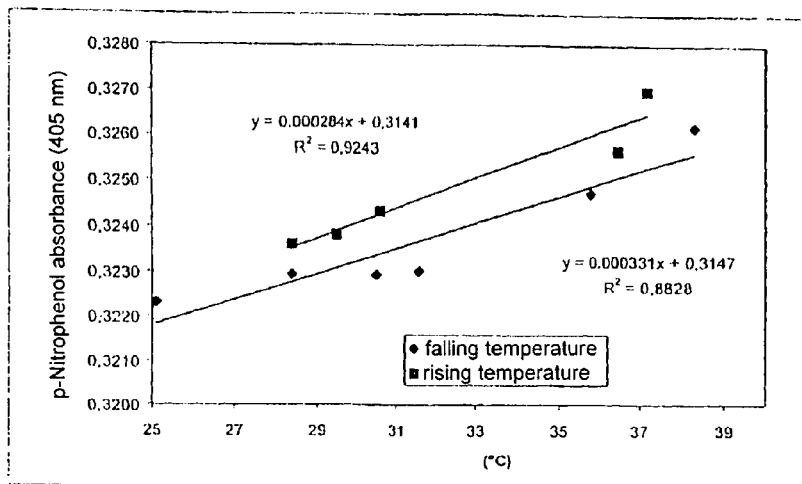
Fig. 3:  Temperature dependence of p-nitrophenol absorbance in phosphate buffer (Application Example 4)
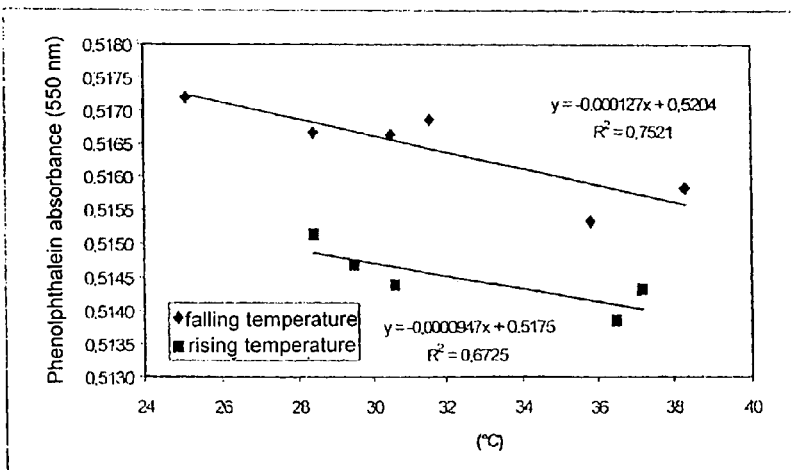
Fig. 4:  Temperature dependence of phenolphthalein absorbance in phosphate buffer (Application Example 4)

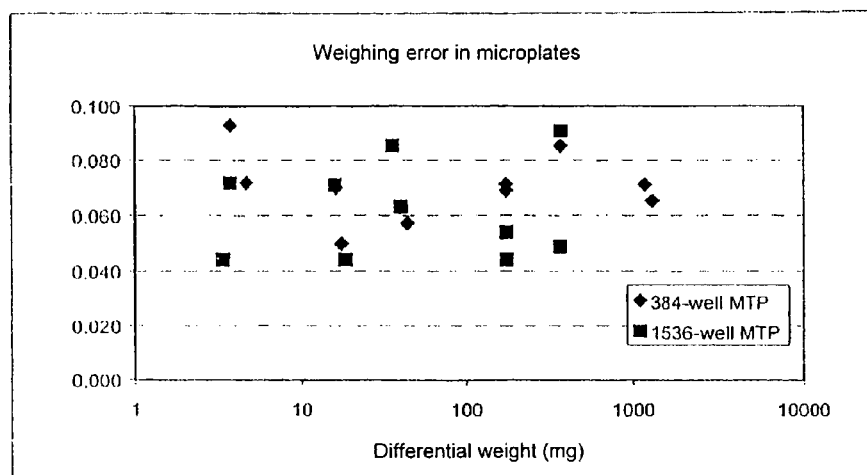
Fig. 5: Standard deviations of different individual masses from 15 individual weighings in microplates (Application Example 9)

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | |
|---|---|---|---|---|---|---|---|---|---|---|---|---|---|---|---|---|---|---|---|---|---|---|---|---|---|
| A | 1.203 | 1.219 | 1.202 | 1.250 | 1.195 | 1.203 | 1.285 | 1.191 | 1.204 | 1.158 | 1.259 | 1.268 | 1.197 | 1.203 | 1.197 | 1.199 | 1.214 | 1.221 | 1.174 | 1.209 | 1.207 | 1.196 | 1.213 | 1.209 | A |
| B | 1.215 | 1.212 | 1.255 | 1.254 | 1.250 | 1.195 | 1.257 | 1.212 | 1.211 | 1.200 | 1.209 | 1.196 | 1.189 | 1.241 | 1.261 | 1.201 | 1.254 | 1.244 | 1.253 | 1.260 | 1.218 | 1.255 | 1.260 | 1.267 | B |
| C | 1.217 | 1.260 | 1.218 | 1.276 | 1.211 | 1.270 | 1.327 | 1.270 | 1.156 | 1.209 | 1.213 | 1.251 | 1.202 | 1.208 | 1.219 | 1.211 | 1.218 | 1.216 | 1.213 | 1.254 | 1.134 | 1.231 | 1.274 | 1.213 | C |
| D | 1.256 | 1.273 | 1.266 | 1.253 | 1.223 | 1.197 | 1.214 | 1.230 | 1.221 | 1.203 | 1.228 | 1.168 | 1.262 | 1.208 | 1.217 | 1.215 | 1.183 | 1.271 | 1.203 | 1.273 | 1.215 | 1.230 | 1.176 | 1.268 | D |
| E | 1.255 | 1.248 | 1.205 | 1.213 | 1.264 | 1.212 | 1.215 | 1.211 | 1.209 | 1.209 | 1.258 | 1.226 | 1.202 | 1.297 | 1.219 | 1.221 | 1.193 | 1.232 | 1.221 | 1.219 | 1.228 | 1.269 | 1.279 | 1.190 | E |
| F | 1.247 | 1.214 | 1.260 | 1.262 | 1.226 | 1.212 | 1.207 | 1.270 | 1.217 | 1.203 | 1.199 | 1.219 | 1.223 | 1.208 | 1.268 | 1.237 | 1.220 | 1.200 | 1.215 | 1.168 | 1.214 | 1.265 | 1.227 | 1.230 | F |
| G | 1.213 | 1.248 | 1.274 | 1.273 | 1.204 | 1.276 | 1.267 | 1.373 | 1.205 | 1.275 | 1.214 | 1.196 | 1.213 | 1.218 | 1.220 | 1.216 | 1.216 | 1.297 | 1.270 | 1.219 | 1.204 | 1.212 | 1.167 | 1.185 | G |
| H | 1.199 | 1.276 | 1.279 | 1.288 | 1.212 | 1.218 | 1.213 | 1.327 | 1.225 | 1.273 | 1.213 | 1.203 | 1.215 | 1.270 | 1.218 | 1.220 | 1.217 | 1.267 | 1.221 | 1.209 | 1.211 | 1.212 | 1.274 | 1.220 | H |
| I | 1.255 | 1.252 | 1.270 | 1.274 | 1.217 | 1.283 | 1.220 | 1.288 | 1.225 | 1.216 | 1.217 | 1.217 | 1.216 | 1.208 | 1.226 | 1.246 | 1.211 | 1.294 | 1.273 | 1.211 | 1.219 | 1.270 | 1.266 | 1.173 | I |
| J | 1.253 | 1.253 | 1.291 | 1.263 | 1.499 | 1.217 | 1.293 | 1.287 | 1.220 | 1.172 | 1.201 | 1.274 | 1.205 | 1.272 | 1.223 | 1.216 | 1.216 | 1.266 | 1.217 | 1.208 | 1.219 | 1.265 | 1.229 | 1.172 | J |
| K | 1.263 | 1.261 | 1.263 | 1.255 | 1.266 | 1.535 | 1.195 | 1.268 | 1.276 | 1.186 | 1.239 | 1.202 | 1.214 | 1.262 | 1.259 | 1.213 | 1.217 | 1.253 | 1.215 | 1.254 | 1.265 | 1.215 | 1.196 | 1.231 | K |
| L | 1.223 | 1.261 | 1.267 | 1.267 | 1.276 | 1.317 | 1.217 | 1.279 | 1.179 | 1.215 | 1.264 | 1.279 | 1.218 | 1.203 | 1.299 | 1.205 | 1.221 | 1.224 | 1.215 | 1.283 | 1.272 | 1.209 | 1.223 | 1.219 | L |
| M | 1.166 | 1.266 | 1.266 | 1.274 | 1.266 | 1.328 | 1.269 | 1.228 | 1.232 | 1.214 | 1.269 | 1.175 | 1.212 | 1.172 | 1.299 | 1.193 | 1.229 | 1.277 | 1.297 | 1.269 | 1.206 | 1.272 | 1.235 | 1.223 | M |
| N | 1.217 | 1.250 | 1.282 | 1.283 | 1.281 | 1.210 | 1.225 | 1.278 | 1.227 | 1.197 | 1.277 | 1.146 | 1.210 | 1.222 | 1.263 | 1.210 | 1.216 | 1.219 | 1.165 | 1.220 | 1.211 | 1.236 | 1.233 | 1.219 | N |
| O | 1.207 | 1.253 | 1.263 | 1.263 | 1.213 | 1.234 | 1.299 | 1.273 | 1.295 | 1.281 | 1.199 | 1.208 | 1.271 | 1.284 | 1.222 | 1.300 | 1.362 | 1.282 | 1.248 | 1.212 | 1.202 | 1.172 | 1.273 | 1.277 | O |
| P | 1.262 | 1.276 | 1.263 | 1.215 | 1.226 | 1.259 | 1.275 | 1.268 | 1.152 | 1.213 | 1.281 | 1.185 | 1.202 | 1.192 | 1.197 | 1.206 | 1.207 | 1.255 | 1.156 | 1.162 | 1.152 | 1.203 | 1.263 | 1.202 | P |
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | |

Fig. 6: Matrix presentation of the quotient values A1/A2 for each well of the microplate (Application Example 10)

|   | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |   |
|---|---|---|---|---|---|---|---|---|---|----|----|----|----|----|----|----|----|----|----|----|----|----|----|----|---|
| A | 0.975 | 0.988 | 0.974 | 1.013 | 0.968 | 0.975 | 1.041 | 0.965 | 0.976 | 0.938 | 1.020 | 1.028 | 0.970 | 0.975 | 0.970 | 0.972 | 0.984 | 0.989 | 0.951 | 0.980 | 0.978 | 0.969 | 0.983 | 0.980 | A |
| B | 0.985 | 0.982 | 1.017 | 1.016 | 1.013 | 0.968 | 1.019 | 0.982 | 0.981 | 0.972 | 0.980 | 0.869 | 0.964 | 1.006 | 1.022 | 0.973 | 1.016 | 1.008 | 1.015 | 1.021 | 0.987 | 1.017 | 1.021 | 1.027 | B |
| C | 0.986 | 1.021 | 0.987 | 1.034 | 0.981 | 1.029 | 1.075 | 1.029 | 0.937 | 0.980 | 0.983 | 1.014 | 0.974 | 0.979 | 0.988 | 0.981 | 0.987 | 0.985 | 0.983 | 1.016 | 0.919 | 0.998 | 1.032 | 0.983 | C |
| D | 1.018 | 1.032 | 1.026 | 1.015 | 0.951 | 0.970 | 0.984 | 0.997 | 0.989 | 0.975 | 0.995 | 0.947 | 1.023 | 0.979 | 0.986 | 0.965 | 0.959 | 1.030 | 0.975 | 1.032 | 0.985 | 0.997 | 0.953 | 1.028 | D |
| E | 1.017 | 1.011 | 0.976 | 0.983 | 1.024 | 0.982 | 0.985 | 0.981 | 0.980 | 0.980 | 1.019 | 0.994 | 0.974 | 0.979 | 0.988 | 0.989 | 0.967 | 0.998 | 0.989 | 0.988 | 0.995 | 1.028 | 1.036 | 0.964 | E |
| F | 1.011 | 0.984 | 1.021 | 1.023 | 0.994 | 0.962 | 0.978 | 1.029 | 0.986 | 0.975 | 0.872 | 0.988 | 0.991 | 1.051 | 1.028 | 1.002 | 0.989 | 0.972 | 0.985 | 0.947 | 0.984 | 1.025 | 0.994 | 0.997 | F |
| G | 0.963 | 1.011 | 1.032 | 1.032 | 0.976 | 1.034 | 1.027 | 1.113 | 0.976 | 1.033 | 0.984 | 0.969 | 0.983 | 0.979 | 0.989 | 0.995 | 0.985 | 1.051 | 1.029 | 0.988 | 0.976 | 0.982 | 0.946 | 0.960 | G |
| H | 0.972 | 1.034 | 1.036 | 1.044 | 0.982 | 0.987 | 0.983 | 1.075 | 0.993 | 1.032 | 0.983 | 0.975 | 0.985 | 0.987 | 0.987 | 0.989 | 0.966 | 1.027 | 0.989 | 0.980 | 0.981 | 0.982 | 1.032 | 0.989 | H |
| I | 1.017 | 1.015 | 1.029 | 1.032 | 0.986 | 1.040 | 0.989 | 1.044 | 0.993 | 0.985 | 0.986 | 0.986 | 0.985 | 0.979 | 0.994 | 1.010 | 0.981 | 1.049 | 1.032 | 0.981 | 0.988 | 1.029 | 1.026 | 0.951 | I |
| J | 1.024 | 1.015 | 1.046 | 1.024 | 1.215 | 0.986 | 1.048 | 1.043 | 0.989 | 0.950 | 0.973 | 1.032 | 0.976 | 1.031 | 0.991 | 0.985 | 0.985 | 1.026 | 0.986 | 0.979 | 0.988 | 1.025 | 0.996 | 0.950 | J |
| K | 0.991 | 1.022 | 1.024 | 1.017 | 1.026 | 1.244 | 0.968 | 1.028 | 1.034 | 0.961 | 1.004 | 0.974 | 0.984 | 1.023 | 1.020 | 0.983 | 0.986 | 1.015 | 0.985 | 1.024 | 1.025 | 0.985 | 0.969 | 0.998 | K |
| L | 0.945 | 1.026 | 1.027 | 1.027 | 1.034 | 1.067 | 0.986 | 1.036 | 0.955 | 0.985 | 1.024 | 1.036 | 0.987 | 0.975 | 1.053 | 0.976 | 0.989 | 0.992 | 1.051 | 1.040 | 1.031 | 0.980 | 0.991 | 0.988 | L |
| M | 0.986 | 1.021 | 1.026 | 1.032 | 1.026 | 1.076 | 1.028 | 0.995 | 0.998 | 0.984 | 1.028 | 0.952 | 0.982 | 0.950 | 1.053 | 0.967 | 0.996 | 1.035 | 1.051 | 1.028 | 0.977 | 0.980 | 1.001 | 0.991 | M |
| N | 0.978 | 1.024 | 1.039 | 1.040 | 1.038 | 0.981 | 0.993 | 1.036 | 0.994 | 0.970 | 1.035 | 0.929 | 0.981 | 0.990 | 1.024 | 0.981 | 0.985 | 0.988 | 0.944 | 0.989 | 0.981 | 1.002 | 0.999 | 0.988 | N |
| O | 1.023 | 1.034 | 1.024 | 1.024 | 0.983 | 1.000 | 1.053 | 1.032 | 1.049 | 1.038 | 0.972 | 0.979 | 1.030 | 1.041 | 0.990 | 1.053 | 1.104 | 1.039 | 1.011 | 0.982 | 0.974 | 0.950 | 1.032 | 1.035 | O |
| P | 1.014 | 0.975 | 1.022 | 0.985 | 0.994 | 1.020 | 1.033 | 1.028 | 0.934 | 0.983 | 1.038 | 0.960 | 0.974 | 0.968 | 0.970 | 0.977 | 0.978 | 1.017 | 0.937 | 0.942 | 0.934 | 0.975 | 1.024 | 0.974 | P |
|   | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |   |

Fig. 7: Matrix representation of the sample volume or reagent volume ( l) calculated for each well of the microplate from the mean sample volume or mean reagent volume determined by gravimetry and the relative photometric deviations (Application Example 10)

METHOD FOR CHARACTERIZING A HIGHLY PARALLELIZED LIQUID HANDLING TECHNIQUE USING MICROPLATES AND TEST KIT FOR CARRYING OUT THE METHOD

CROSS-REFERENCE TO RELATED APPLICATIONS

This application claims priority of International Application No. PCT-DE03/00834, filed Mar. 13, 2003 and German Application No. 102 12 557.0, filed Mar. 14, 2002, the complete disclosures of which are hereby incorporated by reference.

BACKGROUND OF THE INVENTION a) Field of the Invention

The invention is directed to a method for characterizing a highly parallelized liquid handling technology using microplates and a test kit for carrying out the method. It is used wherever highly parallelized liquid handling technology is to be characterized with respect to accuracy and precision, particularly when the handled volumes lie within the µl range or sub-µl range and the characterization must be carried out under conditions corresponding to the real operating conditions of the liquid handling technology. Liquid handling technology using a large number of channels for sample handling, e.g., multipipettes with 96,384 or more channels, provides a large number of sample volumes in individual wells of a microplate that are arranged in grids for preparation and evaluation of samples in many channels or storage and transport, etc., thereof. The correctness and accuracy of sample handling is critically important for the quality and usability of the analysis results. For this reason, a check criterion which might be helpful as a measure of quality, as a basis for certification, and the like, becomes increasingly important for the supplier and for the user of such liquid handling technology b) Description of the Related Art In recent years, highly parallelized, extremely miniaturized methods of analysis based on microplate technology have led to the development of a large number of new and effective applications, particularly for target-oriented active ingredients for analysis of genomes and proteomes and for numerous other areas of biotechnology, medicine and environmental research. For the reasons described above, a corresponding highly parallelized technique for many-channel dispensing, reader technology and other technological developments capable of being adapted to the latter which could be characterized in a manner approaching application as closely as possible were created for many-channel handling of samples. Further, the characterization of a large number of individual channels should be practicable, must not require excessive expenditure on analysis and should be sufficiently precise.

As has been well known for a long time with respect to a large quantity of pipettes, gravimetric methods are used for this characterization along with methods which measure the dilution of an analytic signal of a sample by a diluent, this analytic signal being, in itself, easy to track. Examples of signals of this type are optical signals or radioactivity of a sample.

Gravimetric methods are very precise, but are hardly usable for the µl range and sub-µl range insofar as assessments of precision and accuracy are required to fall within a range of better than 0.5%. Further, the use of gravimetric methods is rendered nearly impossible firstly by evaporation, which constitutes a severe hindrance especially within this volume range, and secondly by problems relating to practicability (very many individual channels must now be characterized, whereas previously only 1 to a maximum of 12 channels had to be characterized). Examinations of this kind were previously restricted to relatively large individual volumes (e.g., GIT Laborzeitschrift 11/2001, 1185-86). The realization of conditions approximating those of real application also creates problems for characterization.

Photometric methods for calibrating pipettes were already described in the 1980s. For example, U.S. Pat. No. 4,354,376 describes a kit for calibrating pipettes which is based on the principle of measuring the dilution of dye solutions. U.S. Pat. No. 5,492,673 describes a reagent system for colorimetric calibration of pipettes which uses a special mixture of substances to correct for the path length of the round cells or cuvettes that are used in order to prevent nonlinearities in the measured absorbances as a function of dye concentration brought about by agglomeration and to improve the stability of the proposed reagent kit. The mixture comprises a 2-buffer system, each with a color indicator. These color indicators differ sharply in the position of the wavelengths of the maxima of the light absorption. Further, the mixture contains substances which inhibit aglomerization and improve stability. However, considerable expenditure on correction is required to exclude device-specific influences due to the photometer that is used and due to the cuvettes and influences particularly of the surrounding temperature.

The availability of parallel reader technology invites the characterization of parallelized dispensing technique using this technology, especially since the large number of individual channels to be characterized would otherwise be very difficult to calibrate. However, it must be taken into consideration that reader technology for microplates is based on the principle of vertical photometry; that is, it has no fixed path length for the individual well. The path length is determined by the volume that is used and by the developing meniscus and is subject to considerable variability depending upon the surface characteristics of the analyte and the mechanical conditions under which the microplate is handled. In U.S. Pat. No. 6,188,476, the absorbance of water in the infrared range is made use of to normalize the measured absorbances of the analyte with respect to a uniform path length in order to compensate for uncertainty regarding the path length. However, practical experience shows that although the average path length can be determined by this correction, compensation of the influence of the individual menisci is unsatisfactory.

In the simplest case, when an absorbance-measuring reader is used to measure the sample volume of a channel of the liquid handling technology with n channels, a diluent volume $V_D$ is introduced in the individual wells of the microplate and a sample volume $V_P$ which contains a dye $F_1$ in a concentration $C_{PF1}$ and which is to be determined is added thereto and mixed. The measured n absorbances of the sample solution $A_P$ and the n mixtures $A_M$ are functions of the respective concentrations of solutions and the path length d according to the Beer-Lambert law:

$$A_P = \epsilon_{F1} * C_{PF1} * d_P$$

$$A_M = \epsilon_{F1} * C_{MF1} * d_M,$$

where $C_{MF1}$ is the concentration of dye $F_1$ in the mixture and $\epsilon$ designates the extinction coefficient of the indicator.

The dilution factor $D_F$ $$D_F = C_{MF1}/C_{PF1} = V_P/(V_P+V_D)$$

can be used to determine $V_P$.

$$V_P = V_D*DF/(1-DF) = V_D*C_{MF1}/C_{PF1}/(1-C_{MF1}/C_{PF1}) \quad (1)$$

It can be seen from equation (1) that the precision with which $V_P$ is determined depends upon the precision with which two absorbances are determined in the reader and upon the accuracy of the present volume $V_D$.

The accuracy of the absorbances A measured in the reader depends upon multiplicatively acting (f) and additively acting (a) errors:

$$A = A*f + a.$$

Multiplicatively acting errors are chiefly the path length which varies because of meniscus formation and the temperature-dependent changes in $\epsilon$; additively acting errors are brought about, for example, by the formation of bubbles, which is frequently observed, and by deposits, scratches and fizz or lint which are sometimes observed. These errors, which ultimately influence the analytic results of the volume determination, can be eliminated in large part by multiwavelength photometry. A procedure of this kind is described, for example, for determining temperature in microplates with thermochrome indicators by absorbance measurement (DE 199 28 056). Practical investigations of the variability of the absorbances measured in readers show that while good precision of the relative values of the absorbances in the individual wells of a microplate with respect to the mean of all measured wells (intra-assay precision) is achieved through the use of multiwavelength photometry, the individual values and mean values of the absorbances measured and obtained, respectively, for different plates have unacceptably high deviations.

Further, with regard to the use of reader technology for characterizing multipipettes, it must be taken into consideration that there are presently no readers for microplates with well densities greater than 384 per microplate (particularly 1536 or more wells) which can measure light absorbances with sufficient accuracy.

OBJECT AND SUMMARY OF THE INVENTION

Therefore, it is the primary object of the invention to provide a method by which highly parallelized liquid handling technology, preferably for volumes in the μl range and sub-μl range, can be characterized more economically and with greater exactness with respect to accuracy and precision under conditions which come very close to the prescribed use of this liquid handling technology.

Further, a test kit is to be provided for the practicable implementation of the method.

This object is met in that sample volumes are dispensed in the wells of at least one microplate with the liquid handling technology to be characterized, wherein conditions coming as close as possible to a prescribed use of the liquid handling technology to be characterized and of the microplate are selected with respect to the selection, constitution and amount of sample liquid or reagent liquid (pipetting solution) and diluent and with respect to the dispensing, handling and analysis of the samples.

According to the invention, a mean sample volume or mean reagent volume with respect to the number of channels of the liquid handling technology is determined by gravimetry under conditions of greatly reduced evaporation from all of the sample volumes and reagent volumes of the individual wells that are dispensed simultaneously in the wells of the microplate; every sample volume and reagent volume, each containing for the purpose of optical measurements a first indicator with specific optical characteristics and at least a second indicator with optical characteristics differing from those of the first indicator, is mixed with a diluent which contains the same at least second indicator in a concentration identical to that of the sample volume or reagent volume but which does not contain the first indicator; at least one first optical measurement signal caused by the first indicator is generated and a second optical measurement signal caused by the second indicator is generated in the same way for each well of the microplate that is filled with a mixture of the sample volume or reagent volume and diluent; every first optical measurement signal is scaled or normalized with respect to its intensity by means of the at least second optical measurement signal of the associated well of the microplate for purposes of error compensation, particularly for eliminating influences of the well geometry, the shape of the liquid surface in the well and blank absorbances due to scratches, bubbles and lint, etc.; a mean optical intensity value which is normalized with respect to the quantity of channels of the liquid handling technology to be characterized is formed from all normalized optical measurement signals and the intensity deviation of the corresponding normalized optical measurement signal in relation to the normalized mean optical intensity value is acquired for every well of the microplate; and the volume of every channel of the liquid handling technology to be characterized is determined with reference to the mean sample volume or mean reagent volume determined by gravimetry from the intensity deviation of the corresponding normalized optical measurement signal in relation to the mean optical intensity value.

With the proposed method, a mean value of all sample volumes or reagent volumes dispensed in the microplate simultaneously by the liquid handling technology to be characterized is first determined. This mean sample volume or mean reagent volume is preferably determined by highly accurate, repeated weighing, wherein the dispensing of the sample volumes or reagent volumes by the liquid handling technology can be carried out in empty wells of the microplate and in a microplate whose wells already contain diluent.

Said optical measurement signals and the relative evaluation of the channel-specific intensity deviations from a normalized mean value of optical intensity can also be determined with high accuracy for precise evaluation. The intensities of at least two individual optical measurement signals are measured at different wavelengths for every well of the microplate, the at least second optical measurement signal being used to eliminate the above-mentioned well-oriented interference factors when normalizing the first optical measurement signal. Buffers whose pH values change very slightly or not at all with changes in temperature are preferably used to reduce the possible influence of different temperatures in the individual wells of the microplate due to the temperature dependence of the extinction coefficient $\epsilon$ of the indicators.

With respect to the very exactly determinable mean sample volume and mean reagent volume of all of the sample volumes and reagent volumes dispensed in the microplate by liquid handling technology, the volume accuracy of every channel of the liquid handling technology can be determined with great precision from the intensity deviation of the normalized well-specific optical measurement signal in relation to the normalized mean optical intensity value. The mean sample volume and mean reagent volume are proportional to the mean intensity value of the normalized optical measurement signal, so that the volume deviation and, therefore, also the sample volume determined for every well for characterizing the liquid handling technology can be calculated from the respective channel-oriented intensity deviation of the corresponding normalized optical measurement signal in relation to the mean intensity value of all normalized optical measurement signals.

For purposes of a clear visual characterization of the liquid handling technology, said measurement signal intensity deviations can be presented as so-called false-color presentations in a matrix corresponding to the channel geometry of the liquid handling technology.

Representing the above-mentioned well-specific sample volumes and reagent volumes determined for characterizing the liquid handling technology in a matrix of this kind which corresponds to the channel geometry of the liquid handling technology is also advisable for evaluation.

It is advantageous that the characterization of the liquid handling technology can be carried out under conditions which come very close to a prescribed use of the liquid handling technology and of the microplate with respect to the handling and analysis of samples. These conditions are realized in particular through suitable selection, constitution and volumes of sample liquid and diluent and through adequate dispensing, handling and analysis of samples in themselves. Therefore, the results determined with the method according to the invention are highly relevant not only for producers of liquid handling equipment (the foundations for appropriate standards would be established in this way), but also, owing to the fact that it approximates practical conditions, for users of this liquid handling technology and accordingly also for interpreting analysis results.

Further embodiments of the method according to the invention are indicated in dependent claims 2 to 29.

Further, a special test kit is indicated for advantageously carrying out the method.

The kit comprises handling instructions and at least five prepared solutions ($L_{1a}$, $L_{2a}$, $L_{1f}$, $L_{2f}$, $L_3$) from which the sample volumes and reagent volumes and the diluent can be produced in a manner specific to the application. Two solutions ($L_{1a}$, $L_{2a}$) are provided for photometric measurements and two solutions ($L_{1f}$, $L_{2f}$) are provided for fluorescence measurements. Solutions $L_{1a}$, $L_{1f}$ are parent solutions for the respective first optical indicator and solutions $L_{2a}$, $L_{2f}$ are parent solutions for the respective second optical indicator. Solution $L_3$ is a parent solution for a quasi-temperature-insensitive buffer (0.5 to 1 M phosphate buffer, pH 11.0).

All kit solutions are prepared in highly concentrated form in comparison to the working concentration.

For photometry, solution $L_{1a}$ comprises 30 mM to 300 mM p-nitrophenol in 96% (vol/vol) ethanol and solution $L_{2a}$, comprises 30 mM to 300 mM phenolphthalein in 96% (vol/vol) ethanol.

For fluorimetry, solution $L_{1f}$ comprises 30 mM to 300 mM methylumbelliferone in dimethyl sulfoxide and solution $L_{2f}$ comprises 0.3 mM to 30 mM fluorescein in 0.1 M phosphate buffer pH 11.0.

In the following, the invention will be described more fully with reference to application examples shown in the drawings.

BRIEF DESCRIPTION OF THE DRAWINGS

In the drawings:

FIG. 1 shows the temperature dependence of the absorbance of p-nitrophenol in diethanolamine buffer (Application Example 4);

FIG. 2 shows the temperature dependence of the absorbance of phenolphthalein in diethanolamine buffer (Application Example 4);

FIG. 3 shows the temperature dependence of the absorbance of p-nitrophenol in phosphate buffer (Application Example 4);

FIG. 4 shows the temperature dependence of the absorbance of phenolphthalein in phosphate buffer (Application Example 4);

FIG. 5 shows standard deviations of different individual masses from 15 individual weighings in microplates (Application Example 9);

FIG. 6 shows a representation of the quotient A1/A2 for every well of the microplate in the form of a matrix (Application Example 10); and FIG. 7 shows a representation of the sample volumes and reagent volumes (µl) calculated for every well of the microplate from the mean sample volume and mean reagent volume determined by gravimetry and the relative photometric deviations in the form of a matrix (Application Example 10).

DESCRIPTION OF THE PREFERRED EMBODIMENTS AND EXAMPLES

Application Example 1

A 384-channel dosing device serving as an example for a liquid handling technology is to be characterized under conditions approximating application for its prescribed use by means of absorbance measurements.

First, 384×48 µl of a diluent (solution D, 0.1 M phosphate buffer, pH 11.0 with 0.04 mM phenolphthalein) which was produced from solutions $L_{2a}$ and $L_3$ of a kit in accordance with the handling directions are pipetted into the wells of two 384-well microplates by a precision dosing device, these microplates being covered by a tightly closing cover. The first microplate is used for evaluation of the dosing; the second microplate is used for determining the evaporation loss within the handling period. The two microplates are then weighed in order to determine a dead weight or empty weight $m_1$ of the first microplate and an initial weight $m_a$ of the second microplate.

After weighing, 2 µl of a sample solution P are pipetted into the wells already containing solution D of the first microplate by the 384-channel dosing device to be characterized. Solution P comprises 0.1 M phosphate buffer, pH 11.0, with 0.04 mM phenolphthalein and 0.06 mM p-nitrophenol and was produced from solutions $L_{1a}$, $L_{2a}$ and $L_3$ of the above-mentioned kit according to handling directions.

All of the handling processes for the above-mentioned pipetting of solution P are also carried out with the second microplate for reference, but without actually pipetting the solution P into the wells already containing solution D of the second microplate. Next, the two microplates are weighed again with their covers. The new weight of the first microplate $m_2$ corresponds to the sum of the empty weight ($m_1$) and the added weight ($\Delta m$) caused by the pipetting process minus the evaporation ($m_v$); the new weight (final weight) of the second microplate $m_e$ results from the initial weight $m_a$ minus the weight loss due to the evaporation weight ($m_v$). This gives the following equations:

$$\Delta m = m_2 - m_1 + m_v \text{ and } m_v = m_a - m_e.$$

Further, the density $\xi$ of the pipetting solution (solution P) is determined by weighing with a pycnometer, known per se, and the mean volume $V_P$ of solution P dispensed by pipetting into the wells of the first microplate is calculated with respect to all channels of the 384-well dosing device.

$$V_P = \Delta m/(\xi*384) = (m_2 - m_1 + m_a - m_e)/(\xi*384)$$

The first microplate is agitated in an agitator, known per se, for approximately 60 minutes so that the solutions D and P located in the wells are thoroughly mixed and the absorbances of p-nitrophenol, phenolphthalein and the blank absorbance are subsequently determined by photometric measurements at wavelengths of 405 nm, 540 nm and 620 nm. Quotient $A_{405}/A_{540}$ and differential quotient $(A_{405} - A_{620})/(A_{540} - A_{620})$ are formed from the absorbance values measured for each well of the first microplate at the above-mentioned wavelengths for normalizing the absorbance of the first indicator p-nitrophenol with well-specific added signals for each well. A spreadsheet, known per se, is preferably applied for calculating and further processing these values.

The associated optical mean values are formed from all 384 quotients and differential quotients of the first microplate and the deviation of the quotient value or differential quotient value from the respective optical mean value is acquired for every well. The relative deviations of the channel-specific values from the mean values of the formed quotients and differential quotients are determined in this way. These deviations are proportional to the relative channel-specific deviations of the pipetted channel-specific sample volumes from the mean sample volume of the first microplate determined by gravimetry.

Based on this proportionality, the ratio f=Ik/Im of the photometric intensity deviation of a well (Ik) from the photometric mean intensity (Im) can be related to the ratio f=Vk/Vm of the volume deviation (Vk) of the same channel from the mean volume (Vm). The pipetted volume of every channel then corresponds to Vk=f*Vm.

False-color presentations of said relative deviation from the respective mean value are helpful as a visual evaluation aid for fast, clear assessment.

Application Example 2

Intra-assay precision of the photometric measurement in 384-well microplates for different dye concentrations:

Solutions of different p-nitrophenol concentrations are produced in that a p-nitrophenol parent solution in 0.1 M phosphate buffer (pH 11.0) with 0.04 mM phenolphthalein is gradually diluted by 0.1 M phosphate buffer (pH 11.0) with 0.04 mM phenolphthalein. 50 µl of the p-nitrophenol working solutions in various concentrations are introduced simultaneously into eight different wells of a 384-well microplate by a multichannel dosing device and measured in a reader (SpektraFluor Plus, Tecan) at wavelengths of 405 nm (A1), 540 nm (A2) and 620 nm (A3), where the bandwidth of the filters is ±10.

The intra-assay precision of the respective 8 identical solutions is listed in the following Table 1. The absorbance at 540 nm (A2) lies within the range of 0.44 to 0.46.

It will be seen that the precision is highly dependent upon the absolute absorbance with a VK minimum in the absorbance range of 0.35 to 0.53. The precision is appreciably improved in this range by forming quotients. A further improvement in precision can be achieved by forming differential quotients only at high absorbances. The precisions actually found in the optimal absorbance range indicate the maximum assertion that can be achieved by the method with respect to the precision of the individual channels with the indicated color system and the indicated reader.

TABLE 1

| Parameter | | | | | | | |
|---|---|---|---|---|---|---|---|
| | A1 | | | | | | |
| Mean | 0.064 | 0.266 | 0.349 | 0.442 | 0.534 | 0.719 | 0.817 |
| VK (%) | 1.66 | 2.72 | 0.45 | 1.01 | 0.93 | 2.87 | 3.23 |
| | A1/A2 | | | | | | |
| VK (%) | 2.25 | 0.47 | 0.30 | 0.34 | 0.39 | 0.14 | 0.88 |
| | (A1-A3)/(A2-A3) | | | | | | |
| VK (%) | 5.14 | 0.79 | 0.31 | 0.39 | 0.41 | 0.19 | 0.16 |

Application Example 3

Inter-assay precision of the photometric measurement in 96-well microplates for different dye concentrations:

Solutions of different p-nitrophenol concentrations are produced in that a p-nitrophenol parent solution in 0.1 M phosphate buffer (pH 11.0) with 0.04 mM phenolphthalein is gradually diluted by 0.1 M phosphate buffer (pH 11.0) with 0.04 mM phenolphthalein. 150 µl of the p-nitrophenol work solutions in various concentrations are introduced simultaneously in individual wells of a 96-well microplate on three different days with a multichannel dosing device and measured in the reader at wavelengths of 405 nm (A1), 540 nm (A2) and 620 nm (A3), where the bandwidth of the filters is ±10.

The inter-assay precision of the three assays is shown in the next Table 2. The absorbance at 540 nm (A2) lies within the range of 0.398 to 0.42.

The inter-assay precision shows a clear dependence on the absorbance level with a minimal VK around A=0.5. In the absorbance range from 0.4 to 0.52, there is an appreciable improvement in the measuring precision by quotient formation. However, the results also show that an exact determination of the accuracy (with a deviation ≦0.5%) for multichannel dosing devices in the entire volume range cannot be achieved solely by optical means.

TABLE 2

| | Inter-assay variation coefficient (%) | | |
|---|---|---|---|
| Absorbance (A1) | A1 | A1/A2 | (A1-A3)/(A2-A3) |
| 0.048 | 3.05 | 3.21 | 5.13 |
| 0.43 | 0.82 | 0.70 | 0.82 |
| 0.52 | 0.59 | 0.33 | 0.40 |
| 0.61 | 0.22 | 0.59 | 0.79 |
| 0.68 | 2.67 | 2.85 | 3.06 |

Application Example 4

Temperature dependence of the photometric measurement signals of p-nitrophenol (F1) and phenolphthalein (F2) in different buffer systems:

Both dyes were dissolved in 0.1 M diethanolamine buffer (pH 10) and also in 0.1 M phosphate buffer (pH 11.0) in such a way that an absorbance of about 0.5 is achieved with a path length of 1 cm. These solutions were measured repeatedly at different temperatures in a temperature-regulated photometer (Contron). The temperature was adjusted up and down by a circulating water bath and measured by a thermosensor in the measurement cuvette.

Diethanolamine buffer: The results are shown in FIG. 1 and FIG. 2. FIG. 1 shows the temperature dependence of p-nitrophenol absorbance and FIG. 2 shows that of the phenolphthalein absorbance. It was found that there was a slight temperature-dependent change in the p-nitrophenol absorbance (A1) compared to phenolphthalein. The phenolphthalein absorbance (A2) shows a clear linear drop of an average of 0.0073/K in the range of 28° C. to 37° C. A linear increase in the absorbance quotient A1/A2 of 0.025/k is derived from this.

Phosphate buffer: It was found that in comparison to the diethanolamine buffer there is a slight temperature-dependent linear increase in the p-nitrophenol absorbance of only 0.0003/K (FIG. 3) and a linear decrease in the phenolphthalein absorbance of 0.0001/K (FIG. 4) within the range of 25° C. to 39° C. This is less than one seventieth of the decrease in absorbance of phenolphthalein in diethanolamine buffer. A very slight linear increase in the absorbance quotient of 0.0008/K is derived from this. With a quotient of, e.g., 0.6, the latter value corresponds to a deviation of 0.13%/K and is therefore less than the measurement precision found in known readers.

Application Example 5

Intra-assay precision of the photometric measurement in all wells of 384-well microplates in the absorbance range of the highest precision using A1, quotient A1/A2 and differential quotient (A1−A3)/(A2−A3):

50 μl of a homogeneous mixture comprising 0.06 mM p-nitrophenol and 0.09 mM phenolphthalein were pipetted into the wells of a 384-well microplate with a multichannel dosing device, the plate was briefly agitated and then measured in the reader at 405 nm (A1), 540 nm (A2) and 620 nm (A3).

The mean values, relative deviations, expressed as variation coefficients, were calculated for the absorbance value A1 of all wells and for their normalized values from A1/A2 and (A1−A3)/(A2−A3) and determined for each individual well. The results are compiled in Table 3. It will be seen that the precision is appreciably improved through normalization by means of quotients. The forming of differential quotients does not result in a further increase in precision in this case.

TABLE 3

| Parameter | Microplate | A1 | A2 | A1/A2 | (A1−A3)/(A2−A3) |
|---|---|---|---|---|---|
| Mean | 1 | 0.705 | 0.560 | 1.26 | 1.26 |
| SD |  | 0.075 | 0.054 | 0.00 | 0.00 |
| VK |  | 1.06 | 0.96 | 0.26 | 0.26 |
| Mean | 2 | 0.700 | 0.553 | 1.27 | 1.28 |
| SD |  | 0.068 | 0.054 | 0.00 | 0.01 |
| VK |  | 0.97 | 0.98 | 0.33 | 0.39 |

Application Example 6

Intra-assay precision of the fluorimetric measurement using Flu1 and quotient Flu1/Flu2:

50 μl of a homogeneous mixture comprising 0.06 mM methylumbelliferone and 1.3 μM fluorescein were pipetted into the wells of a 1536-well microplate by a multichannel dosing device, the plate was briefly agitated and then measured in a reader at 460 nm (Flu1, excitation 365 nm) and 535 nm (Flu2, excitation 485 nm).

The mean values, standard deviations and variation coefficients were calculated for the fluorescence values Flu1 and Flu2 of all wells and for their normalized values from Flu1/Flu2. The results are compiled in Table 4. The considerable improvement in precision through the formation of quotients can be seen in this case also. The precision of the quotients shows the maximum precision that can be achieved by the respective reader and, therefore, the resolution of the method.

TABLE 4

| Parameter | Microplate | Flu1 | Flu2 | Flu1/Flu2 |
|---|---|---|---|---|
| Mean | 1 | 5370.51 | 8142.27 | 0.660 |
| SD |  | 384.41 | 578.92 | 0.008 |
| VK |  | 7.16 | 7.11 | 1.19 |
| Mean | 2 | 5410.47 | 8331.78 | 0.650 |
| SD |  | 551.92 | 866.15 | 0.008 |
| VK |  | 10.20 | 10.40 | 1.20 |

Application Example 7

Intra-assay precision of pipetting of 384 sample volumes using measurement signals A1 and quotient A1/A2.

Different volumes, indicated in column 2 of the following Table 5, of the sample solutions P comprising p-nitrophenol in the concentrations indicated in column 1 of Table 5 and, in addition, 0.04 mM phenolphthalein were dispensed in the wells of 384-well microplates by a multichannel dosing device to be checked. For this purpose, volumes of a solution D of 0.04 mM phenolphthalein in 0.1 M phosphate buffer (pH 11.0) were distributed in the individual wells by another precision multichannel dosing device in such a way that the total volume in every well was 50 μl. The microplates were tightly closed with adhesive foils and agitated for 60 minutes. The absorbances were then measured in the reader at wavelengths of 405 nm (A1) and 540 nm (A2).

The mean values, standard deviations and variation coefficients (VK) were calculated for the absorbance values A1 and A2 of all wells and for their normalized values from A1/A2. The results are compiled in Table 5.

The precisions normalized by forming quotients are better in all cases than the precisions calculated by exclusive use of A1 and therefore represent the dosing accuracy better than the measurement of A1 exclusively.

TABLE 5

| Solution P | | | | | |
|---|---|---|---|---|---|
| p-Nitrophenol concentration (mM) | Reference volume (μl) | Parameter | A1 | A2 | Quotient A1/A2 |
| 0.3 | 10 | Mean | 0.566 | 0.455 | 1.245 |
|  |  | SD | 0.007 | 0.004 | 0.008 |
|  |  | VK | 1.194 | 0.906 | 0.667 |
| 0.3 | 10 | Mean | 0.565 | 0.494 | 1.144 |
|  |  | SD | 0.005 | 0.003 | 0.008 |
|  |  | VK | 0.823 | 0.702 | 0.719 |
| 0.6 | 5 | Mean | 0.568 | 0.498 | 1.14 |
|  |  | SD | 0.008 | 0.006 | 0.015 |
|  |  | VK | 1.348 | 1.237 | 1.324 |
| 0.6 | 5 | Mean | 0.549 | 0.49 | 1.117 |
|  |  | SD | 0.006 | 0.005 | 0.012 |
|  |  | VK | 1.183 | 1.029 | 1.045 |

Application Example 8

Intra-assay precision of pipetting of 384 sample volumes using Flu1 and quotient Flu1/Flu2:

Sample solutions comprising methylumbelliferone and 2 μM fluorescein in 0.1 M diethanolamine buffer (pH 9.8) were dispensed in the wells of 384-well microplates by a multichannel dosing device to be characterized. The methylumbelliferone concentration is variable and is given in column 1 of Table 6; the volume is given in column 2. In addition, different volumes of a solution of 2 µM fluorescein in 0.1 M diethanolamine buffer (pH 9.8) were pipetted in the wells of the microplates by another precise multichannel dosing device. These volumes were selected in such a way that a final volume of 50 µl resulted. The microplates were agitated for 60 minutes and then measured in a reader at wavelengths of 460 nm (Flu1, excitation 365 nm) and 535 nm (Flu2, excitation 485 nm).

The mean values, standard deviations and variation coefficients were calculated for the fluorescence value Flu1 of all wells and for their normalized value from Flu1/Flu2. The results are compiled in Table 6. It will be noted that the precision is mostly improved after forming quotients.

TABLE 6

| Methyl-umbelliferone concentration (Mm) | Reference volume (µl) | Parameter | Flu1 | Flu2 | Quotient Flu1/Flu2 |
|---|---|---|---|---|---|
| 0.6 | 5 | Mean | 18447.6 | 25000 | 0.738 |
|  |  | SD | 391.7 | 503.9 | 0.014 |
|  |  | VK | 2.12 | 2.01 | 1.89 |
| 0.6 | 5 | Mean | 18266 | 25376 | 0.720 |
|  |  | SD | 368.4 | 498.9 | 0.012 |
|  |  | VK | 2.02 | 1.966 | 1.67 |
| 3 | 1 | Mean | 17581 | 24983 | 0.704 |
|  |  | SD | 608.7 | 604.8 | 0.025 |
|  |  | VK | 3.46 | 2.42 | 3.58 |
| 3 | 1 | Mean | 18131 | 25096 | 0.723 |
|  |  | SD | 586.5 | 593.4 | 0.023 |
|  |  | VK | 3.24 | 2.36 | 3.17 |

Application Example 9

Precision of weighing: Various dry individual masses were determined 15 times by a precision scale using microplates with 384 wells and 1536 wells as carriers. The standard deviations from 15 individual weighings for different individual masses are compiled in FIG. 5. For weighing with the microplate empty weight, for 384-well microplates of about 56 g and for 1536-well microplates of about 34 g, there is a mean standard deviation in the weighing for individual masses within the range of 5-1300 mg of 0.0699 mg and 0.0618 mg (FIG. 5).

When weighing in microplates, the standard deviation is relatively constant and not dependent upon the individual mass (FIG. 5).

This means that there are different relative errors, albeit very slight (compare Table 7), for different pipetted individual volumes. In the extreme case (384 times 0.05 µl sample volume in 384-well microplates), there is a mean error of less than 0.4%; for all other volumes, appreciably smaller errors in weighing accuracy are to be expected. Therefore, the weighing error due to scale inaccuracies is negligible within the volume ranges and mass ranges being examined. Therefore, weighing is the method of choice for determining dosing accuracy.

TABLE 7

Computational error in weighing differential weights in microplates (MP)

| Individual dosing volumes | Total dosing volume per plate (µl ≙ mg) | | Computational error due to weighing inaccuracy (% of total dosed volume) | |
|---|---|---|---|---|
| (µl) | 384-well MP | 1536-well MP | 384-well MP | 1536-well MP |
| 0.05 | 19.2 | 76.8 | 0.3642 | 0.0805 |
| 0.1 | 38.4 | 153.6 | 0.1821 | 0.0403 |
| 0.2 | 76.8 | 307.2 | 0.0911 | 0.0201 |
| 0.5 | 192 | 768 | 0.0364 | 0.0081 |
| 0.7 | 268.8 | 1075.2 | 0.0260 | 0.0058 |
| 1 | 384 | 1536 | 0.0182 | 0.0040 |
| 2 | 768 | 3072 | 0.0091 | 0.0020 |

Application Example 10

Evaluation of the accuracy and precision of a 384-channel dosing device:

The method principle applied in Application Example 1 is used. Two pipetter variants a and b approximating application are evaluated in parallel with 1 µl being dosed by way of example.

Pipetter variant a: Solution P is pipetted into a dry microplate. 49 µl of solution D are dispensed subsequently in all wells.

Pipetter variant b: Solution P is pipetted into a microplate filled with 49 µl of solution D.

Solution P comprises 0.04 mM phenolphthalein and 3 mM p-nitrophenol in dimethyl sulfoxide; solution D comprises 0.04 mM phenolphthalein and 0.1 M phosphate buffer (pH 11.0).

The procedure and the results of the gradual steps are shown in Table 8 and in FIG. 6 and FIG. 7.

TABLE 8

| Variant a | Variant b | Variant a | Variant b |
|---|---|---|---|
| Step 1 | | Assertion | |
|  | 49 µl of a solution D are pipetted into the wells of two 384-well MPs which are covered by a tightly closing cover |  |  |
| The empty MP with cover is weighed 1 µl of solution P is pipetted into the dry wells of the MPs | MP1 and MP2 are weighed with covers 1 µl of solution P is pipetted into the filled wells of MP1 with the dosing | $m_1$: 69.0718 g | $m_1$ (MP1): 87.9158 g $m_a$ (MP2): 87.8633 g |

TABLE 8-continued

| Variant a | Variant b | Variant a | Variant b |
|---|---|---|---|
| | device to be tested; parallel identical handling of MP2, but without pipetting | | |
| The MPs are weighed again with covers | Both Mps are weighed again with covers, cover of MP 1 is then replaced with adhesive foil | $m_2$: 69.4895 g<br>$\Delta m = m_2 - m_1 =$<br>417.7 mg | $m_2(MP1)$: 88.3232 g<br>$M_e(MP2)$: 87.8516 g<br>$\Delta m = m_2 - m_1 + m_\upsilon =$<br>419.1 mg<br>$m_\upsilon$: 11.7 mg |
| 49 μl of solution D are pipetted into the wells, covered with adhesive foil | | | |
| Near-time determination of density $\xi$ of pipetting solution<br>Empty weight of pycnometer: 38.5644 g<br>Weight of pycnometer filled with solution P: 43.9929 g | | Differential weight for 5.0 ml pycnometer contents: 5.4285 g<br>Density $\xi = 1.0857$ g/ml | |
| Calculation of mean actual volume | | (69.4895 g − 69.0718 g)/<br>(1.0857 g/ml * 384) =<br>1.0019 μl | (88.3232 g − 87.9158 g +<br>87.8633 g − 87.8516 g)/<br>(1.0857 g/ml * 384) =<br>1.0053 μl |
| Mixture MP | Mixture MP1 | | |
| | | Step 2 | |
| MP is measured in a reader at 405 nm and 540 nm | MP1 is measured in a reader at 405 nm and 540 nm | | |
| | Quotient ($A_{405}/A_{540}$) formed for the associated absorbances of every well | | |
| | | Step 3 | |
| Mean MP value taken from all 384 quotients (photometric mean intensity) and the relative deviation of every well value from the photometric plate averages is calculated | | Mean value: 1.234<br>SD: 0.041<br>VK: 3.35 | Mean value: 1.342<br>SD: 0.028<br>VK: 2.07 |

FIGS. 6 and 7 show a false-color presentation of the relative deviation from the photometric plate average and the actual dosing volume derived therefrom for every well of the microplate 1 and, therefore, for every associated channel of the dosing device.

FIG. 6 represents the quotient A1/A2 for every well and FIG. 7 represents the dosing volume calculated from the mean sample volume determined by gravimetry and the channel-specific relative photometric deviations.

In FIGS. 6 and 7, a medium box color represents a well whose value deviation lies within the range of the plate average ±1 of the standard deviation; a light box color represents a well whose value deviation deviates downward by more than 1 SD from the plate average; a dark box color represents well values showing values that deviate upward by more than 1 SD from the plate average.

While the foregoing description and drawings represent the present invention, it will be obvious to those skilled in the art that various changes may be made therein without departing from the true spirit and scope of the invention.

What is claimed is:

1. A method for characterizing highly parallelized liquid handling technology, preferably for volumes in the μl range and sub-μl range, using microplates, wherein the liquid handling technology has a large number of elements for sample handling, such as multipipettes, by which a large number of sample volumes of a sample liquid or reagent liquid are placed in wells of a microplate that are arranged in grids for preparation and analysis or storage and transport, etc., of samples in many channels with determination of volumes by gravimetry and optical measurement in the presence of a diluent, comprising the steps of:

determining a mean sample volume or mean reagent volume with respect to the number of channels of the liquid handling technology by gravimetry under conditions of greatly reduced evaporation from all of the sample volumes or reagent volumes that are dispensed simultaneously into the wells of the microplate by the liquid handling technology to be characterized;

mixing every sample volume and reagent volume, each containing a first indicator with specific optical characteristics and at least one second indicator with optical characteristics differing from those of the first indicator for purposes of optical measurements, with a diluent which contains the same at least second indicator in a concentration identical to that of the sample volume or reagent volume but which does not contain the first indicator;

generating at least one first optical measurement signal caused by the first indicator and, in the same way, a second optical measurement signal caused by the second indicator for each well of the microplate that is filled with a mixture of the sample volume or reagent volume and diluent;

normalizing every first optical measurement signal with respect to its intensity by the at least second optical measurement signal of the associated well of the microplate for purposes of error compensation, particularly for eliminating influences of the well geometry, the shape of the liquid surface in the well, the blank absorbances, etc.;

forming a mean optical intensity value which is normalized with respect to the quantity of channels of the liquid handling technology to be characterized from all normalized optical measurement signals and the intensity deviation of the corresponding normalized optical measurement signal from the normalized mean optical intensity value is acquired for every well of the microplate; and determining the volume of every channel of the liquid handling technology to be characterized with reference to the mean sample volume or mean reagent volume determined by gravimetry from the intensity deviation of the corresponding normalized optical measurement signal in relation to the mean optical intensity value.

2. The method according to claim 1, wherein the mean sample volume or mean reagent volume is determined by repeated weighing, wherein the density of the sample volumes or reagent volumes is known.

3. The method according to claim 2, wherein the weighing is carried out before mixing the sample volumes or reagent volumes with the diluent.

4. The method according to claim 2, wherein the weighing is carried out after mixing the sample volumes or reagent volumes with the diluent.

5. The method according to claim 1, wherein the dispensing of the sample volumes or reagent volumes by the liquid handling technology to be characterized into the wells of the microplate is carried out in a steam-saturated chamber in order to create conditions of greatly reduced evaporation.

6. The method according to claim 1, wherein the microplate is closed, for example, by a cover or by a foil, so as to be protected against evaporation after the sample volumes are dispensed into its wells.

7. The method according to claim 1, wherein the dispensing of the sample volumes or reagent volumes by the liquid handling technology to be characterized is carried out in the wells of a closed microplate whose closure can be perforated.

8. The method according to claim 1, wherein a loss of mass occurring as a result of evaporation is continuously determined by weighing, and wherein the loss of mass and the course of evaporation over time is deduced by extrapolation from the initial volume, preferably using computation technology.

9. The method according to claim 1, wherein the dispensing of the sample volumes or reagent volumes by the liquid handling technology to be characterized is carried out in empty wells of the microplate, and wherein the diluent volumes are pipetted into the latter subsequently.

10. The method according to claim 1, wherein the dispensing of the sample volumes or reagent volumes by the liquid handling technology to be characterized is carried out in wells of the microplate in which the diluent volumes have already been introduced.

11. The method according to claim 1, wherein an aqueous solution is used as sample liquid or reagent liquid.

12. The method according to claim 1, wherein a solution of organic solvent is used as sample liquid or reagent liquid.

13. The method according to claim 11, wherein a mixture of organic solvents and aqueous solutions is used as sample liquid or reagent liquid.

14. The method according to claim 1, wherein an aqueous solution is used as diluent.

15. The method according to claim 1, wherein a solution of organic solvent is used as diluent.

16. The method according to claim 1, wherein a mixture of organic solvents and aqueous solutions is used as diluent.

17. The method according to claim 1, wherein additional reagents such as buffers, saline solutions, protein-containing solutions, cell suspensions, particle solutions and different solvent proportions are added to the sample liquid or reagent liquid and/or to the diluent.

18. The method according to claim 17, wherein a phosphate buffer with a pH of 9.0-12.5 which is virtually independent from temperature with respect to its pH value is added as a buffer.

19. The method according to claim 1, wherein dyes are used as indicators in the sample liquid or reagent liquid or in the diluent.

20. The method according to claim 19, wherein p-nitrophenol and phenolphthalein are used as dyes.

21. The method according to claim 20, wherein p-nitrophenol, as first indicator, is added only to the sample liquid or reagent liquid, and wherein phenolphthalein, as second indicator, is added in an identical concentration to the sample liquid or reagent liquid and to the diluent.

22. The method according to claim 19, wherein the normalized optical measurement signal is generated based on the formation of the quotient from the first optical measurement signal absorbance A1 and the second optical measurement signal absorbance A2 (A1/A2) in the wavelength range of 390-420 nm (A1) and in the wavelength range of 530 to 560 nm (A2).

23. The method according to claim 19, wherein the normalized optical measurement signal is generated based on the formation of the differential quotient from the first optical measurement signal absorbance A1 and the second optical measurement signal absorbance A2 and the third optical measurement signal absorbance A3 ((A1−A3)/(A2−A3)) in the wavelength range of 390-420 nm (A1), in the wavelength range of 530 to 560 nm (A2), and in the wavelength range of 620-890 nm (A3).

24. The method according to claim 19, wherein fluorescent dyes are used as dyes for the indicators.

25. The method according to claim 24, wherein methylumbelliferone, as first indicator, is added only to the sample liquid or reagent liquid, and wherein fluorescein, as second indicator, is added in an identical concentration to the sample liquid or reagent liquid and to the diluent.

26. The method according to claim 24, wherein the normalized optical measurement signal is generated based on the formation of the quotient (Flu1/Flu2) from the first optical measurement signal (fluorescence Flu1) and the second optical measurement signal (fluorescence Flu2) for normalizing the fluorescence intensities at 440-470 nm (excitation at 340-370 nm, Flu1) and the fluorescence intensities at 520-550 nm (excitation at 470-500 nm, Flu2).

27. The method according to claim 1, wherein the intensity deviations of the normalized first optical measurement signals of every well of the microplate from the optical mean intensity are presented as a false-color presentation in a matrix corresponding to the channel geometry of the liquid handling technology for purposes of a clear visual evaluation.

28. The method according to claim 1, wherein and the pipetting volumes of every well of the microplate which are determined for determining the volume accuracy for characterizing the liquid handling technology are presented in a matrix corresponding to the channel geometry of the liquid handling technology.

29. The method according to claim 1, wherein with respect to type, volume and added reagents of sample liquid or reagent liquid and diluent, with respect to the dispensing of samples into dry wells or into liquids, and with respect to the handling of samples in the microplates themselves, conditions are realized which come as close as possible to a prescribed use of the liquid handling technology to be characterized and of the microplate.

* * * * *